United States Patent [19]

Hoehn

[11] 4,169,205
[45] Sep. 25, 1979

[54] IMIDAZOLE DERIVATIVES OF 6,11-DIHYDRODIBENZ[B,E]OXEPINES AND 6,11-DIHYDRODIBENZ[B,E]THIEPINES

[75] Inventor: Hans Hoehn, Tegernheim, Fed. Rep. of Germany

[73] Assignee: E. R. Squibb & Sons, Inc., Princeton, N.J.

[21] Appl. No.: 954,729

[22] Filed: Oct. 25, 1978

[51] Int. Cl.² ............... C07D 405/04; C07D 409/04
[52] U.S. Cl. ............................. 548/336; 424/273 R
[58] Field of Search ........................... 548/336, 345

[56] References Cited

U.S. PATENT DOCUMENTS

| 3,275,640 | 9/1966 | Engelhardt et al. | 546/202 |
| 3,647,816 | 3/1972 | Draber et al. | 548/336 |
| 3,764,609 | 10/1973 | van der Stelt | 548/345 |
| 3,778,447 | 12/1973 | Draber et al. | 548/345 |
| 4,021,561 | 5/1977 | Remy et al. | 546/202 |
| 4,049,418 | 9/1977 | Timmler et al. | 548/345 |
| 4,112,112 | 9/1978 | Rooney et al. | 424/274 |

FOREIGN PATENT DOCUMENTS 1299246 12/1972 United Kingdom ............... 548/345

OTHER PUBLICATIONS

Stach et al., Monatshefte für Chemie, 1962, vol. 93, pp. 889–895.
Winthrop et al., J. Med. Pharm. Chem., 1962, vol. 5, pp. 1207–1213.
Kluge et al., Current Abstracts of Chemistry, 1978, vol. 70, Abstract No. 273247.

*Primary Examiner*—Natalie Trousof
*Attorney, Agent, or Firm*—Lawrence S. Levinson

[57] ABSTRACT

New imidazole derivatives of 6,11-dihydrodibenz[b,e]oxepines and 6,11-dihydrodibenz[b,e]thiepines have the general formula

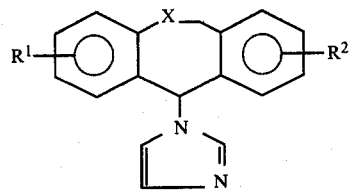

They and the salts thereof are useful as antifungal and antibacterial agents.

13 Claims, No Drawings

IMIDAZOLE DERIVATIVES OF 6,11-DIHYDRODIBENZ[B,E]OXEPINES AND 6,11-DIHYDRODIBENZ[B,E]THIEPINES

SUMMARY OF THE INVENTION

This invention relates to new imidazole derivatives of 6,11-dihydrodibenz[b,e]oxepines and 6,11-dihydrodibenz[b,e]thiepines as well as salts thereof. These new compounds have the general formula

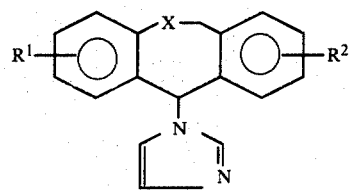

wherein
X is oxygen or sulfur;
$R^1$ and $R^2$ each is hydrogen, halogen, trifluoromethyl, lower alkyl, hydroxy, lower alkoxy, lower alkylthio, nitro or the basic group

wherein $R^3$ and $R^4$ each is independently hydrogen, lower alkyl, phenyl or substituted phenyl wherein the phenyl bears one halogen, hydroxy, lower alkoxy, lower alkyl, lower alkylthio, cyano or nitro group.

DETAILED DESCRIPTION OF THE INVENTION

In formula I the lower alkyl groups include straight or branched chain hydrocarbon groups containing 1 to 7 carbon atoms. Examples of the type of groups contemplated are methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio. In all of these radicals the $C_1$–$C_4$, especially the $C_1$–$C_2$ members, are preferred.

The halogens are the four common halogens, chlorine and bromine being preferred in that order. Preferably, but not necessarily, the $R^1$ and $R^2$ substituents in a single compound are the same. The substituted phenyl groups refer to phenyl rings bearing one of the simple substituents named, which are of the same character as described above. Unsubstituted phenyl is preferred.

The basic nitrogen groups

include, for example, amino; lower alkylamino, e.g., methylamino, ethylamino, propylamino and the like; di(lower alkyl)amino, e.g., dimethylamino, diethylamino, methylethylamino, dipropylamino, dibutylamino and the like; phenylamino; diphenylamino; 2-, 3- or 4-chlorophenylamino; 2-, 3- or 4-hydroxyphenylamino; (lower alkoxyphenyl)amino, e.g., 2-, 3- or 4-methoxyphenylamino; (lower alkylphenyl)amino, e.g., 2-, 3- or 4-methylphenylamino; (lower alkylthiophenyl)amino, e.g., (2-, 3- or 4-methylthio)-phenylamino; 2-, 3- or 4-cyanophenylamino or 2-, 3- or 4-nitrophenylamino.

Preferred embodiments of the invention are compounds of formula I wherein X is oxygen or sulfur and $R^1$ and $R^2$ each is hydrogen or halogen. Especially preferred are those compounds of formula I wherein both $R^1$ and $R^2$ are hydrogen or $R^2$ is hydrogen and $R^1$ is other than hydrogen, particularly halogen, most especially chlorine, and most particularly chlorine in the 2-position. The hydrohalide salts and especially the hydrochloride salt, are also preferred.

The compounds of formula I are prepared by N-cycloalkylation of an imidazole of the formula

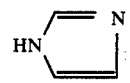

with an appropriate reactive ester of the formula

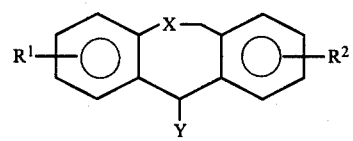

wherein Y is a reactive ester function, such as halo, mesyl, tosyl or the like.

The reactive ester intermediates of formula III are generally prepared by converting the corresponding alcohol of the formula

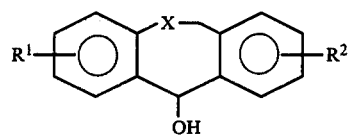

into the desired reactive ester according to methods generally known in the art.

A preferred method, which can be effected without isolating the ester of formula III, is the direct reaction of an alcohol of formula IV with thionyl-bis-imidazole or carbonyl-bis-imidazole of the formula

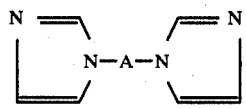

wherein A represents —SO— or —CO—.

The alcohols of formula IV are prepared by reduction of the corresponding tricyclic ketones [J. Med. Chem. 5, 1210 (1962); Monatshefte d. Chem. 93, 892 (1962)].

Additional experimental details are found in the illustrative examples below.

The compounds of formula I form salts which are also part of this invention. The salts include acid-addition salts, particularly the non-toxic, physiologically acceptable members. The compounds of formula I form salts by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt in the appropriate medium in which the salt is insoluble, then after separation of the salt, neutralizing with a base such as barium hydroxide or sodium hydroxide, to obtain the free base of formula I. Other salts may then be formed from the free base by reaction with an equivalent of acid having the desired anion.

The new compounds of formula I and their salts are useful as antimicrobial agents, particularly as antifungal agents, and can be used to combat infections in various mammalian species, such as mice, rats, dogs, guinea pigs and the like, due particularly to organisms such as *Candida albicans* as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg/kg/day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc. as called for by accepted pharmaceutical practice. Preferably they are applied topically, e.g., intravaginally in a lotion or in a conventional cream base at a concentration of about 0.01 to 3 percent by weight for a period of 3 to 7 days, 2 to 4 times daily.

The following examples are illustrative of the invention. They represent particularly preferred embodiments and also serve as models for the preparation of other members of the group. All temperatures are on the Celsius scale.

EXAMPLE 1

1-(6,11-Dihydrodibenz[b,e]oxepin-11-yl)-1H-imidazole

To a solution of 4.2 g. of 11-hydroxy-6,11-dihydrodibenz[b,e]oxepine (0.02 mol.) in 125 ml. of anhydrous benzene is added 6.5 g. of N,N'-carbonyl-bis-imidazole (0.04 mol.). In order to get the N,N'-carbonyl-bis-imidazole completely dissolved, the mixture is heated for a short time to 60°–65°. The solution is allowed to stand for 24 hours at room temperature. After the benzene is removed, the residual 1-(6,11-dihydrodibenz[b,e]oxepin-11-yl)-1H-imidazole is treated with water, filtered off, washed with water and ether, dried and recrystallized from acetonitrile, yield 4.3 g. (82%), m.p. 154°–155°.

EXAMPLE 2

1-(2-Chloro-6,11-dihydrodibenz[b,e]oxepin-11-yl)-1H-imidazole 2.5 g. of 2-chloro-11-hydroxy-6,11-dihydrodibenz[b,e]oxepine (0.01 mol.) dissolved in 60 ml. of anhydrous benzene are reacted with 3.25 g, of N,N'-carbonyl-bis-imidazole (0.02 mol.) according to the procedure of Example 1 to obtain 1-(2-chloro-6,11-dihydrodibenz[b,e]oxepin-11-yl)-1H-imidazole, yield 1.2 g. (41%), m.p. 180°–182° (acetonitrile).

EXAMPLE 3

1-(6,11-Dihydrodibenz[b,e]thiepin-11yl)-1H-imidazole 5.7 g. of 11-hydroxy-6,11-dihydrodibenz[b,e]thiepine (0.025 mol.) dissolved in 150 ml. of anhydrous benzene and 8.1 g. of N,N'-carbonyl-bis-imidazole are reacted according to the procedure of Example 1 to obtain 1-(6,11-dihydrodibenz[b,e]thiepin-11-yl)-1H-imidazole; yield 3.7 g. (08%), m.p. 162°–164° (acetonitrile).

The hydrochloride salt is obtained by treating the above product with an excess of ethereal hydrochloric acid and recrystallizing from acetonitrile.

EXAMPLE 4

1-(2-Chloro-6,11-dihydrodibenz[b,e]thiepin-11-yl)-1H-imidazole 5.2 g. of 2-chloro-11-hydroxy-6,11-dihydrodibenz[b,e]thiepine (0.02 mol.) dissolved in 200 ml. of anhydrous benzene and 6.5 g. of N,N'-carbonyl-bis-imidazole are reacted according to the procedure of Example 1 to obtain 1-(2-chloro-6,11-dihydrodibenz[b,e]thiepin-11-yl)-1H-imidazole; yield 4.1 g. (65.5%), m.p. 175°–176° (acetonitrile).

The following additional compounds are produced by the procedure of Example 1 or Example 3, by substituting for the 11-hydroxy-6,11-dihydrodibenz[b,e]oxepine or the 11-hydroxy-6,11-dihydrodibenz[b,e]thiepine, respectively, the $R^1$ and/or $R^2$-substituted analog.

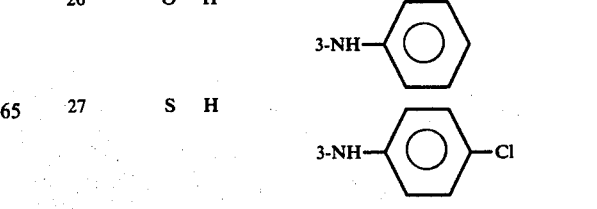

| Example | X | $R^2$ | $R^1$ |
|---|---|---|---|
| 5 | O | H | 3-$CF_3$ |
| 6 | O | H | 2-$CF_3$ |
| 7 | S | H | 3-$CF_3$ |
| 8 | S | H | 2-$CF_3$ |
| 9 | O | 8-Cl | 3-Cl |
| 10 | O | 9-Br | 3-BR |
| 11 | S | H | 3-Cl |
| 12 | O | H | 4-Cl |
| 13 | O | 9-$CH_3$ | H |
| 14 | S | H | 3-$OCH_3$ |
| 15 | O | H | 2-$OC_2H_5$ |
| 16 | O | H | 3-$SCH_3$ |
| 17 | S | H | 3-$SCH_3$ |
| 18 | S | H | 4-$C_2H_5$ |
| 19 | O | H | 2-$NO_2$ |
| 20 | S | H | 3-$NO_2$ |
| 21 | O | H | 3-$NHCH_3$ |
| 22 | S | H | 3-$NHCH_3$ |
| 23 | O | H | 2-$NHC_2H_5$ |
| 24 | S | H | 3-$N(CH_3)_2$ |
| 25 | O | H | 2-$N(CH_3)_2$ |
| 26 | O | H | 3-NH—⌬ |
| 27 | S | H | 3-NH—⌬—Cl |

-continued

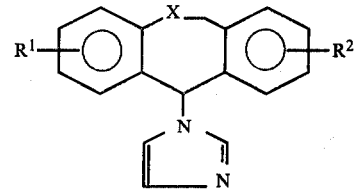

| Example | X | R² | R¹ |
|---------|---|-----|-----|
| 28 | O | H | 2-NH—⟨phenyl⟩—OH |
| 29 | S | H | 3-NH—⟨phenyl⟩—OCH₃ (ortho) |
| 30 | O | H | 2-NH—⟨phenyl⟩—CH₃ |
| 31 | O | H | 2-NH—⟨phenyl⟩—SCH₃ |
| 32 | S | H | 2-NH—⟨phenyl⟩—CN |
| 33 | O | H | 3-NH—⟨phenyl⟩—NO₂ |
| 34 | O | H | 3-NH₂ |
| 35 | S | H | 2-NH |
| 36 | O | 8-OH | H |
| 37 | S | 9-OH | H |
| 38 | O | H | 2-OH |
| 39 | S | H | 3-OH |

What is claimed is:

1. A compound of the formula

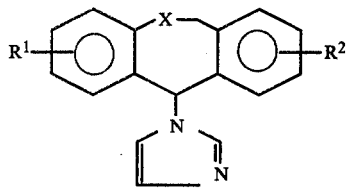

wherein
X is oxygen or sulfur;
R¹ and R² each is hydrogen, halogen, hydroxy, trifluoromethyl, lower alkyl, lower alkoxy, lower alkylthio, nitro or the group $$-N\begin{array}{c}R^3\\ \\R^4\end{array};$$

R³ and R⁴ each is hydrogen, lower alkyl, phenyl or substituted phenyl wherein the phenyl bears one halogen, hydroxy, lower alkoxy, lower alkyl, lower alkylthio, cyano or nitro;

and non-toxic, physiologically acceptable acid addition salts thereof.

2. A compound as in claim 1 wherein R¹ is hydrogen or halogen and R² is hydrogen.
3. A compound as in claim 1 wherein R¹ and R² each is hydrogen or halogen.
4. A compound as in claim 1 wherein R¹ and R² each is hydrogen.
5. A compound as in claim 1 wherein R¹ is halogen and R² is hydrogen.
6. A compound as in claim 5 wherein the halogen is chlorine.
7. A compound as in claim 1 wherein R¹ is

and R³ and R⁴ each is hydrogen, lower alkyl or phenyl.
8. A compound as in claim 1 wherein X is oxygen.
9. A compound as in claim 1 wherein X is sulfur.
10. A compound as in claim 1 wherein X is oxygen; R¹ is 2-chloro; and R² is hydrogen.
11. A compound as in claim 1 wherein X is oxygen and R¹ and R² each is hydrogen.
12. A compound as in claim 1 wherein X is sulfur and R¹ and R² each is hydrogen.
13. A compound as in claim 1 wherein X is sulfur; R¹ is 2-chloro; and R² is hydrogen.

* * * * *

UNITED STATES PATENT AND TRADEMARK OFFICE
CERTIFICATE OF CORRECTION

PATENT NO. : 4,169,205
DATED : September 25, 1979
INVENTOR(S) : Hans Hoehn

It is certified that error appears in the above-identified patent and that said Letters Patent are hereby corrected as shown below:

In column 6, claim 7 should read:
--7. A compound as in Claim 1 wherein $R^1$ is $-N\begin{matrix}R^3\\R^4\end{matrix}$  and $R^3$ and $R^4$ each is hydrogen, lower alkyl or phenyl.--

Signed and Sealed this

Twenty-third Day of September 1980

[SEAL]

Attest:

SIDNEY A. DIAMOND

Attesting Officer

Commissioner of Patents and Trademarks